United States Patent [19]

Wenderoth et al.

[11] Patent Number: 5,334,577
[45] Date of Patent: Aug. 2, 1994

[54] OXIME ETHER DERIVATIVES, THEIR PREPARATION AND FUNGICIDES CONTAINING THESE DERIVATIVES

[75] Inventors: Bernd Wenderoth, Lampertheim; Siegbert Brand, Weinheim; Franz Schuetz, Ludwigshafen; Thomas Kuekenhoehner, Frankenthal; Franz Roehl; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 620,456

[22] Filed: Dec. 4, 1990

Related U.S. Application Data

[63] Continuation of Ser. No. 411,638, Sep. 25, 1989, abandoned.

[30] Foreign Application Priority Data

Oct. 14, 1988 [DE] Fed. Rep. of Germany ....... 3835028

[51] Int. Cl.⁵ .................. C07D 263/58; A01N 43/76
[52] U.S. Cl. ..................... 504/130; 546/286; 546/287; 546/288; 546/290; 546/296
[58] Field of Search ................... 71/94; 546/286, 287, 546/288, 290, 296

[56] References Cited

U.S. PATENT DOCUMENTS

| 4,322,241 | 3/1982 | Pissiotas et al. | 71/94 |
| 4,334,912 | 6/1982 | Yoshida et al. | 71/94 |
| 4,347,372 | 8/1982 | Föry et al. | 546/290 X |

FOREIGN PATENT DOCUMENTS

| 0254426 | 1/1988 | European Pat. Off. |
| 0278595 | 8/1988 | European Pat. Off. |
| 0253213 | 12/1988 | European Pat. Off. |
| 0299694 | 1/1989 | European Pat. Off. |

*Primary Examiner*—Johann Richter
*Assistant Examiner*—Catherine S. Kilby Scalzo
*Attorney, Agent, or Firm*—Oblon, Spivak, McClelland, Maier & Neustadt

[57] ABSTRACT

Oxime ether derivatives of the formula I

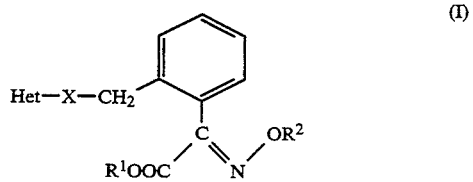

where $R^1$ and $R^2$ are each hydrogen or alkyl, Het is pyridyl, quinolyl, pyrimidinyl, pyrazinyl, pyridazinyl, thienyl, quinoxalinyl, isoxazolyl, benzoxazolyl or benzothiazolyl, the heterocyclic ring system being unsubstituted or substituted, and X is oxygen or sulfur, their plant-tolerated acid addition salts, metal complexes and N-oxides, and fungicides containing these compounds.

6 Claims, No Drawings

OXIME ETHER DERIVATIVES, THEIR PREPARATION AND FUNGICIDES CONTAINING THESE DERIVATIVES

This application is a continuation of application Ser. No. 07/411,638 filed on Sep. 25, 1989, now abandoned.

The present invention relates to novel oxime ether derivatives, their preparation, fungicides containing these derivatives and their use as fungicides.

It is known that oxime ethers, for example methyl 2-(phenoxymethyl)-phenylglyoxylate O-methyloxime, can be used as fungicides (European Patent 253,213 and 254,426). However, their fungicidal action is often unsatisfactory.

We have found that substituted oxime ether derivatives of the general formula I

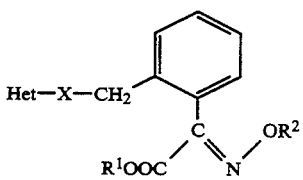

(I)

where $R^1$ and $R^2$ are each hydrogen or $C_1$–$C_5$-alkyl, Het is pyridyl, quinolyl, pyrimidinyl, pyrazinyl, pyridazinyl, thienyl, guinoxalinyl, isoxazolyl, benzoxazolyl or benzothiazolyl, the heterocyclic ring system being unsubstituted or substituted by halogen, $C_1$–$C_8$-alkyl, $C_3$–$C_6$-cycloalkyl, $C_1$- or $C_2$-haloalkyl, $C_1$–$C_4$-alkoxy, $C_1$–$C_4$-alkoxy-$C_1$–$C_4$-alkyl, aryl, aryl-$C_1$–$C_4$-alkyl, $C_1$–$C_4$-alkylcarbonyl, $C_1$–$C_4$-alkoxycarbonyl or cyano, and X is oxygen or sulfur, and their plant-tolerated acid addition salts, metal complexes and N-oxides have an excellent fungicidal action.

The radicals stated for the general formula I may have, for example, the following meanings. $R^1$ and $R^2$ are identical or different and are each hydrogen or $C_1$–$C_5$-alkyl, such as methyl, ethyl, propyl, isopropyl, butyl or pentyl.

Het may be, for example, 2-pyridyl, 3-pyridyl, 4-pyridyl, 2-quinolyl, 3-quinolyl, 4-quinolyl, 8-quinolyl, 2-pyrimidinyl, 4-pyrimidinyl, 5-pyrimidinyl, 2-pyrazinyl, 3-pyridazinyl, 2-thienyl, 3-thienyl, 2-quinoxalinyl, 5-isoxazolyl, 2-benzoxazolyl or 2-benzothiazolyl, and the heterocyclic ring system may be unsubstituted or substituted by one to three of the following radicals: halogen (e.g. fluorine, chlorine or bromine), $C_1$–$C_8$-alkyl (e.g. methyl, ethyl, n-propyl, isopropyl, n-butyl, iso-butyl, sec-butyl, tert-butyl, n-pentyl, isopentyl, sec-pentyl, tert-pentyl, neopentyl, hexyl, heptyl or octyl), $C_3$–$C_6$-cycloalkyl (e.g. cyclopropyl, cyclobutyl, cyclopentyl, cyclohexyl), $C_1$- or $C_2$-haloalkyl (e.g. difluoromethyl, trifluoromethyl, chloromethyl, dichloromethyl, trichloromethyl or pentafluoroethyl), $C_1$–$C_4$-alkoxy (e.g. methoxy, ethoxy, n-propoxy, isopropoxy, n-butoxy, isobutoxy, sec-butoxy or tert-butoxy), $C_1$–$C_4$-alkoxy-$C_1$–$C_4$-alkyl (e.g. methoxymethyl, ethoxymethyl, methoxyethyl or propoxymethyl), aryl (e.g. phenyl), aryl-$C_1$–$C_4$-alkyl (e.g. benzyl, 2-phenylethyl, 3-phenylpropyl or 4-phenylbutyl), $C_1$–$C_4$-alkylcarbonyl (e.g. acetyl, ethylcarbonyl, propylcarbonyl or butylcarbonyl), $C_1$–$C_4$-alkoxycarbonyl (e.g. methoxycarbonyl, ethoxycarbonyl, propoxycarbonyl or butoxycarbonyl) or cyano.

X is oxygen or sulfur.

The novel compounds can also be converted into plant-tolerated acid addition salts of the inorganic or organic acids by reaction with acids, for example into salts of hydrochloric acid, hydrobromic acid, nitric acid, oxalic acid, acetic acid, sulfuric acid or phosphoric acid or dodecylbenzenesulfonic acid. The activity of the salts is due to the cation, so that any anion may in general be chosen.

Furthermore, the novel compounds can be converted into metal complexes by known method8. This may be done by reacting these compounds with metal salts, for example with the metals copper, zinc, iron, manganese or nickel, e.g. copper (II) chloride, zinc (II) chloride, iron (III) chloride, copper (II) nitrate, manganese (II) chloride or nickel (II) bromide.

If the novel compounds are reacted with oxidizing agents, for example with m-chloroperbenzoic acid, the N-oxides of the heterocyclic compounds are obtained.

Because of the C=N double bond, the novel compounds of the formula I may be obtained in their preparation in the form of E/Z isomer mixtures, which can be separated into the individual components in a conventional manner, for example by crystallization or chromatography. Both the individual isomeric compounds and their mixtures are embraced by the invention and can be used as fungicides.

The novel compounds of the general formula I can be prepared, for example, by reacting a heterocyclic compound of the formula Het—X—H (II), with a benzyl halide of the general formula III (Hal=Cl, Br or I).

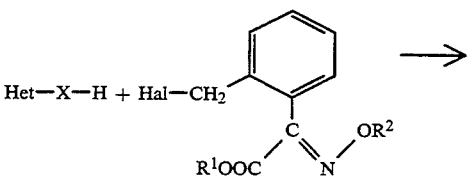

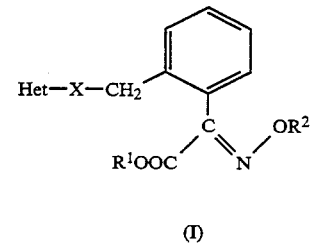

(II)  (III)

(I)

The reactions to give the compounds of the formula I can be carried out, for example, in an inert solvent or diluent (e.g. acetone, acetonitrile, dimethyl sulfoxide, dioxane, dimethylformamide, N-methylpyrrolidone, N,N'-dimethylpropyleneurea or pyridine) with the use of a base (e.g. sodium carbonate or potassium carbonate). It may also be advantageous to add a catalyst, e.g. tris-(3,6-dioxoheptyl)-amine, to the reaction mixture (J. Org. Chem. 50 (1985), 3717).

In an alternative procedure, a compound of the general formula II can first be converted into the corresponding sodium or potassium salt with a base (e.g. sodium hydroxide or potassium hydroxide) and the said salt can then be reacted with a benzyl halide of the formula III in an inert solvent or diluent (e.g. dimethylformamide) to give the corresponding compound of the general formula I.

The heterocyclic starting compounds of the general formula Het-X-H (where Het and X have the abovementioned meanings) are either known or can be prepared by processes similar to known processes. Appropriate preparation processes are described in, for example, European Patent 224,217, German Patent 2,531,035, J. Heterocycl. Chem. 20 (1983), 219 and ibid. 24 (1987), 709.

The ortho-substituted benzyl halides of the formula III can be prepared by halogenating conventional $\alpha$-ketocarboxylates of the formula IV (cf. for example B. J. M. Photis, Tetrahedron Lett. 1980, 3539) at the methyl group by a method known from the literature.

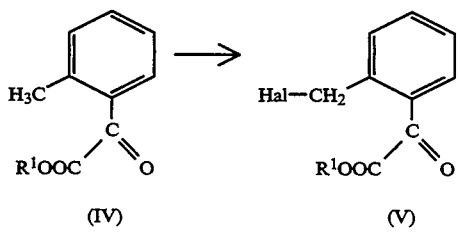

(IV)  (V)

Using bromine or chlorine in a solvent, such as tetrachloromethane, with or without exposure to a light source (for example a 300 W Hg vapor lamp) and with N-chloro- or N-bromosuccinimide (Horner and Winkelmann, Angew. Chem. 71 (1959), 349), for example, $\alpha$-ketocarboxylates of the general formula V, where $R^1$ has the above-mentioned meanings are obtained.

The halides of the formula III can be prepared by reacting an $\alpha$-ketocarboxylate of the formula V, for example, a) with an O-substituted hydroxylamine of the formula $H_2N$—$OR^2$, where $R^2$ has the abovementioned meanings, or b) with hydroxylamine to give the corresponding oxime and then reacting the product with an alkyl halide of the formula $R^2$-Hal, where $R^2$ has the abovementioned meanings and Hal is a halogen atom (F, Cl, Br or I), or with a dialkyl sulfate.

The halides of the formula III can also be prepared by reacting an $\alpha$-ketocarboxylate of the formula IV, for example, a) with an O-substituted hydroxylamine of the formula $H_2N$—$OR^2$, where $R^2$ has the abovementioned meanings, or b) with hydroxylamine to give the corresponding oxime and then reacting the product with an alkyl halide of the formula $R^2$-Hal, where $R^2$ has the abovementioned meanings and Hal is a halogen atom (F, Cl, Br or I), or with a dialkyl sulfate to give the oxime ether derivative of the general formula VI, where $R^1$ and $R^2$ each have the abovementioned meanings.

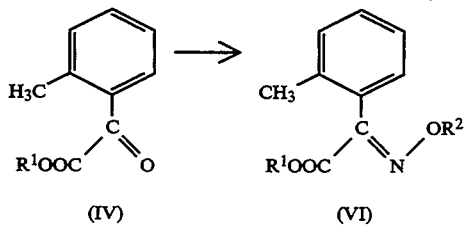

(IV)  (VI)

The compounds of the formula VI can then be converted into the halides of the formula III by halogenation at the methyl group by a method known from the literature. This is done, for example, using bromine or chlorine in a solvent, such as tetrachloromethane, with or without exposure to a light source (for example a 300 W Hg vapor lamp) and with N-chloro- or with N-bromosuccinimide (Horner and Winkelmann, Angew. Chem. 71 (1959), 349).

The novel compounds of the formula I can also be prepared, for example, by reacting a novel $\alpha$-ketocarboxylate of the formula VII

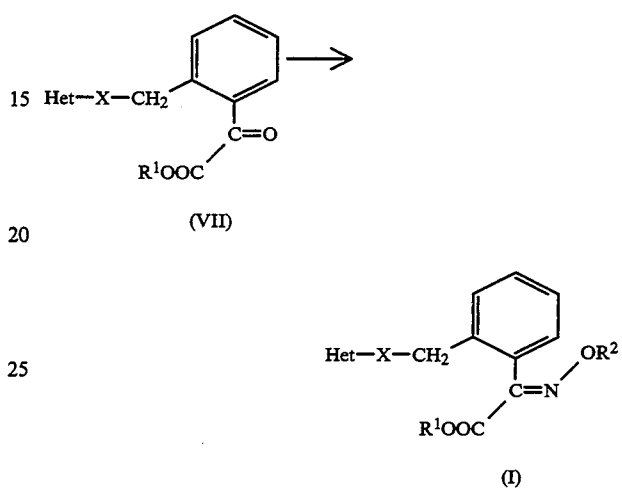

(VII)

(I)

a) with an O-substituted hydroxylamine of the formula $H_2NOR^2$, where $R^2$ has the abovementioned meanings, or b) with hydroxylamine to give the corresponding oxime and then reacting the product with an alkyl halide of the formula $R^2$—Hal, where $R^2$ has the abovementioned meanings and Hal is a halogen atom (F, Cl, Br or I), or with a dialkyl sulfate.

The novel $\alpha$-ketocarboxylates of the general formula VII are useful intermediates. They can be prepared, for example, by reacting the abovementioned compound of the formula V with a heterocyclic compound of the formula II.

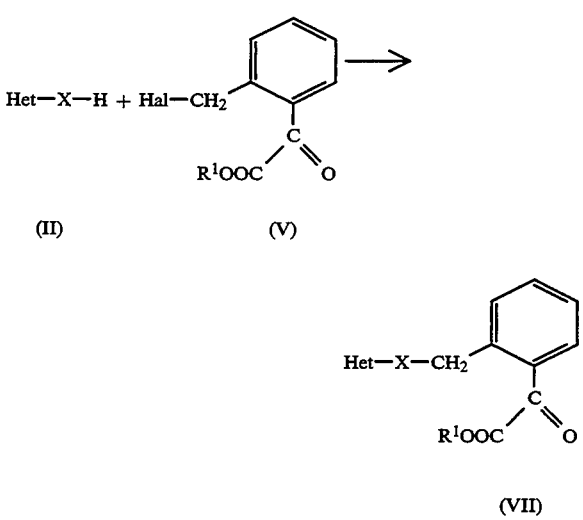

(II)  (V)

(VII)

The reactions to give the compounds of the formula VII can be carried out, for example, in an inert solvent or diluent (e.g. acetone, acetonitrile, dimethyl sulfoxide, dioxane, dimethylformamide, N-methylpyrrolidone, N,N'-dimethylpropyleneurea or pyridine) with the use of a base (e.g. sodium carbonate or potassium carbonate). It may also be advantageous to add a catalyst, e.g. tris-(3,6-dioxoheptyl)-amine to the reaction mixture (J. Org. Chem. 50 (1985), 3717).

In an alternative procedure, a compound of the general formula II can first be converted into the corresponding sodium or potassium salt with a base (e.g. sodium hydroxide or potassium hydroxide) and the said salt can then be reacted with a benzyl halide of the formula V in an inert solvent or diluent (e.g. dimethylformamide) to give a novel α-ketocarboxylate of the general formula VII.

EXAMPLES

The Examples which follow illustrate the preparation of the novel active ingredients of the general formula I.

METHOD 1

Preparation of methyl 2-(bromomethyl)-phenylglyoxylate 5.34 g (30 millimoles) of methyl 2-methylphenylglyoxylate and 5.34 g (30 millimoles) of N-bromosuccinimide in 1000 l of tetrachloromethane are exposed to a 300 W Hg vapor lamp for one hour. The organic phase is then washed once with water and three times with sodium bicarbonate solution and is dried over sodium sulfate/sodium carbonate. After the solution has been evaporated down, the crude product is chromatographed over silica gel using 1:9 methyl tert-butyl ether/n-hexane. 3.8 g (49%) of the abovementioned compound are obtained as a yellow oil.

$^1$H-NMR (CDCl$_3$): d=3.97 (s, 3H), 4.90 (s, 2H), 7.4–7.8 (m, 4H).

IR (film), 2955, 1740, 1689, 1435, 1318, 1207, 999 cm$^{-1}$

METHOD 2

Preparation of methyl 2-(chloromethyl)-phenylglyoxylate 100 g (0.56 mole) of methyl 2-methylphenylglyoxylate in 600 ml of tetrachloromethane are initially taken. The mixture is then refluxed while being exposed to a 300 W Hg vapor lamp, and 28 g (0.39 mole) of chlorine gas are passed in during this procedure. After a conversion of about 50% (determined by thin-layer chromatography), the reaction is terminated and the mixture is evaporated down. The residue is then subjected to fractional distillation. 29 g of product were obtained as an oil.

$^1$H-NMR (CDCl$_3$): d=3.97 (s, 3H), 5.0 (s, 2H), 7.4–7.8 (m, 4H).

METHOD 3

Preparation of methyl 2-(bromomethyl)-phenylglyoxylate O-methyloxime 21.4 g (0.133 mole) of bromine are added with stirring to 27.5 g (0.133 mole) of methyl 2-methylphenylglyoxylate O-methyloxime, dissolved in 400 ml of tetrachloromethane. The mixture is then refluxed for four hours while being exposed to a 300 W Hg vapor lamp. It is then evaporated down, the residue is taken up in ethyl acetate/water and the solution is washed with H$_2$O, dried with sodium sulfate and evaporated down. The crude product is purified by chromatography over silica gel using 9:1 cyclohexane/ethyl acetate. 17.4 g (46%) of the abovementioned compound are obtained as an oil.

$^1$H (CDCl$_3$): δ=3.88 (s, 3H), 4.08 (s, 3H), 4.33 (s, 2H), 6.12–7.52 (m, 4H).

EXAMPLE 1

Preparation of methyl 2-[(6'-methyl-2'-pyridyl)-oxymethyl]-phenylglyoxylate O-methyloxime (compound no. 2)

4.85 g (37 millimoles) of the sodium salt of 2-hydroxy-6-methylpyridine are initially taken together with 0.1 g of potassium iodide in 100 ml of absolute N,N-dimethylformamide. 5.3 g (18.5 millimoles) of methyl 2-(bromomethyl)-phenylglyoxylate O-methyloxime, dissolved in 50 ml of absolute N,N-dimethylformamide, are then added dropwise at room temperature (20° C.), while stirring. After stirring has been continued for 5 hours at 100° C., the mixture is evaporated down and the residue is taken up in ethyl acetate. The solution is washed with H$_2$O, dried over sodium sulfate and evaporated down. The crude product is crystallized by trituration with n-pentane. The crystals are isolated and dried. 1.2 g (21% yield) of the abovementioned compound (mp.=67°–72° C.) are obtained.

$^1$H-NMR (CDCl$_3$): δ=2.41 (s, 3H), 3.83 (s, 3H), 4.02 (s, 3H), 5.22 (s, 2H), 6.47 (d, 1H), 6.67 (d, 1H), 7.18–7.60 (m, 5H).

The compounds shown in the Table below can be prepared in a similar manner.

TABLE 1

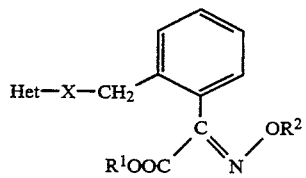

| No. | Het | X | R$^1$ | R$^2$ | mp (°C.) | IR (cm$^{-1}$) |
| --- | --- | --- | --- | --- | --- | --- |
| 1 | 2-pyridyl | S | CH$_3$ | CH$_3$ | | |
| 2 | 6-methyl-2-pyridyl | O | CH$_3$ | CH$_3$ | 67–72 | 2940, 1742, 1601, 1580, 1456, 1305, 1227, 1070, 1101 |
| 3 | 6-methyl-2-pyridyl | S | CH$_3$ | CH$_3$ | 104–108 | |
| 4 | 6-ethyl-2-pyridyl | O | CH$_3$ | CH$_3$ | | |
| 5 | 6-ethyl-2-pyridyl | S | CH$_3$ | CH$_3$ | 68–70 | |
| 6 | 6-n-propyl-2-pyridyl | O | CH$_3$ | CH$_3$ | | |
| 7 | 6-n-propyl-2-pyridyl | S | CH$_3$ | CH$_3$ | | |
| 8 | 6-iso-propyl-2-pyridyl | O | CH$_3$ | CH$_3$ | 63–67 | 1731, 1459, 1441, 1069, 1011, 805, 777 |

TABLE 1-continued

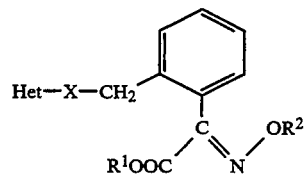

| No. | Het | X | R¹ | R² | mp (°C.) | IR (cm$^{-1}$) |
|---|---|---|---|---|---|---|
| 9 | 6-iso-propyl-2-pyridyl | S | CH₃ | CH₃ | 60–63 | |
| 10 | 6-n-butyl-2-pyridyl | O | CH₃ | CH₃ | | |
| 11 | 6-n-butyl-2-pyridyl | S | CH₃ | CH₃ | | |
| 12 | 6-tert.-butyl-2-pyridyl | O | CH₃ | CH₃ | 73–75 | 1724, 1443, 1313, 1259, 1071, 1019, 803 |
| 13 | 6-tert.-butyl-2-pyridyl | S | CH₃ | CH₃ | 98–103 | |
| 14 | 6-n-pentyl-2-pyridyl | O | CH₃ | CH₃ | | |
| 15 | 6-n-pentyl-2-pyridyl | S | CH₃ | CH₃ | | |
| 16 | 6-n-hexyl-2-pyridyl | O | CH₃ | CH₃ | | |
| 17 | 6-n-hexyl-2-pyridyl | S | CH₃ | CH₃ | | |
| 18 | 6-phenyl-2-pyridyl | O | CH₃ | CH₃ | | |
| 19 | 6-phenyl-2-pyridyl | S | CH₃ | CH₃ | | |
| 20 | 6-benzyl-2-pyridyl | O | CH₃ | CH₃ | | |
| 21 | 6-benzyl-2-pyridyl | S | CH₃ | CH₃ | | |
| 22 | 6-trifluoromethyl-2-pyridyl | O | CH₃ | CH₃ | | |
| 23 | 6-trifluoromethyl-2-pyridyl | S | CH₃ | CH₃ | | |
| 24 | 6-methoxy-2-pyridyl | O | CH₃ | CH₃ | | |
| 25 | 6-methoxy-2-pyridyl | S | CH₃ | CH₃ | | |
| 26 | 6-chloro-2-pyridyl | O | CH₃ | CH₃ | | |
| 27 | 6-chloro-2-pyridyl | S | CH₃ | CH₃ | 106 | 1740, 1592, 1442, 1032, 1059, 1009, 774 |
| 28 | 3,6-dimethyl-2-pyridyl | O | CH₃ | CH₃ | | |
| 29 | 3,6-dimethyl-2-pyridyl | S | CH₃ | CH₃ | | |
| 30 | 3,6-diethyl-2-pyridyl | O | CH₃ | CH₃ | | |
| 31 | 3,6-diethyl-2-pyridyl | S | CH₃ | CH₃ | | |
| 32 | 4,6-dimethyl-2-pyridyl | O | CH₃ | CH₃ | | |
| 33 | 4,6-dimethyl-2-pyridyl | S | CH₃ | CH₃ | | |
| 34 | 5,6-dimethyl-2-pyridyl | O | CH₃ | CH₃ | | |
| 35 | 5,6-dimethyl-2-pyridyl | S | CH₃ | CH₃ | | |
| 36 | 4-phenyl-6-methyl-2-pyridyl | O | CH₃ | CH₃ | | |
| 37 | 4-phenyl-6-methyl-2-pyridyl | S | CH₃ | CH₃ | | |
| 38 | 4,6-diphenyl-2-pyridyl | O | CH₃ | CH₃ | | |
| 39 | 4,6-diphenyl-2-pyridyl | S | CH₃ | CH₃ | | |
| 40 | 3,4-dichloro-6-methyl-2-pyridyl | O | CH₃ | CH₃ | | |
| 41 | 3,4-dichloro-6-methyl-2-pyridyl | S | CH₃ | CH₃ | | |
| 42 | 3,4,5-trichloro-6-phenyl-2-pyridyl | O | CH₃ | CH₃ | | |
| 43 | 3,4,5-trichloro-6-phenyl-2-pyridyl | S | CH₃ | CH₃ | | |
| 44 | 4-trifluoromethyl-6-methyl-2-pyridyl | O | CH₃ | CH₃ | | |
| 45 | 4-trifluoromethyl-6-methyl-2-pyridyl | S | CH₃ | CH₃ | | |
| 46 | 3-acetyl-4,6-dimethyl-2-pyridyl | O | CH₃ | CH₃ | | |
| 47 | 3-acetyl-4,6-dimethyl-2-pyridyl | S | CH₃ | CH₃ | | |
| 48 | 3-cyano-6-methyl-2-pyridyl | O | CH₃ | CH₃ | 132–135 | 2215, 1729, 1594, 1061, 1013, 760 |
| 49 | 3-cyano-6-methyl-2-pyridyl | S | CH₃ | CH₃ | | |
| 50 | 3-cyano-6-ethyl-2-pyridyl | O | CH₃ | CH₃ | 87–90 | |
| 51 | 3-cyano-6-ethyl-2-pyridyl | S | CH₃ | CH₃ | | |
| 52 | 3-cyano-6-n-propyl-2-pyridyl | O | CH₃ | CH₃ | | |
| 53 | 3-cyano-6-n-propyl-2-pyridyl | S | CH₃ | CH₃ | | |
| 54 | 3-cyano-6-iso-propyl-2-pyridyl | O | CH₃ | CH₃ | | |
| 55 | 3-cyano-6-iso-propyl-2-pyridyl | S | CH₃ | CH₃ | | |
| 56 | 3-cyano-6-cyclo-propyl-2-pyridyl | O | CH₃ | CH₃ | | |
| 57 | 3-cyano-6-cyclo-propyl-2-pyridyl | S | CH₃ | CH₃ | | |
| 58 | 3-cyano-6-n-butyl-2-pyridyl | O | CH₃ | CH₃ | | |
| 59 | 3-cyano-6-n-bytyl-2-pyridyl | S | CH₃ | CH₃ | | |
| 60 | 3-cyano-6-tert.-butyl-2-pyridyl | O | CH₃ | CH₃ | | |
| 61 | 3-cyano-6-tert.-butyl-2-pyridyl | S | CH₃ | CH₃ | | |
| 62 | 3-cyano-6-cyclo-hexyl-2-pyridyl | O | CH₃ | CH₃ | | |
| 63 | 3-cyano-6-cyclo-hexyl-2-pyridyl | S | CH₃ | CH₃ | | |
| 64 | 3-cyano-6-phenyl-2-pyridyl | O | CH₃ | CH₃ | 123–125 | 2315, 1727, 1591, 1456, 1220, 1065, 1019, 771 753 |
| 65 | 3-cyano-6-phenyl-2-pyridyl | S | CH₃ | CH₃ | | |
| 66 | 3-methyloxycarbonyl-6-iso-propyl-2-pyridyl | O | CH₃ | CH₃ | | |
| 67 | 3-methyloxycarbonyl-6-iso-propyl-2-pyridyl | S | CH₃ | CH₃ | | |
| 68 | 3-ethyloxycarbonyl-6-iso-propyl-2-pyridyl | O | CH₃ | CH₃ | | |
| 69 | 3-ethyloxycarbonyl-6-iso-propyl-2-pyridyl | S | CH₃ | CH₃ | | |
| 70 | 3-cyano-4,6-dimethyl-2-pyridyl | O | CH₃ | CH₃ | | |
| 71 | 3-cyano-4,6-dimethyl-2-pyridyl | S | CH₃ | CH₃ | | |
| 72 | 3,5,6-trichloro-2-pyridyl | O | CH₃ | CH₃ | | |
| 73 | 3,5,6-trichloro-2-pyridyl | S | CH₃ | CH₃ | | |
| 74 | 5-trifluoromethyl-2-pyridyl | O | CH₃ | CH₃ | | |

TABLE 1-continued

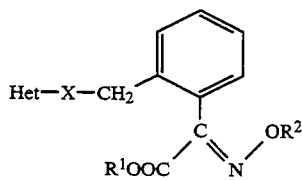

| No. | Het | X | $R^1$ | $R^2$ | mp (°C.) | IR (cm$^{-1}$) |
|---|---|---|---|---|---|---|
| 75 | 5-trifluoromethyl-2-pyridyl | S | CH$_3$ | CH$_3$ | | |
| 76 | 3-chloro-5-trifluoromethyl-2-pyridyl | O | CH$_3$ | CH$_3$ | | |
| 77 | 3-chloro-5-trifluoromethyl-2-pyridyl | S | CH$_3$ | CH$_3$ | | |
| 78 | 2-quinolyl | O | CH$_3$ | CH$_3$ | | |
| 79 | 2-quinolyl | S | CH$_3$ | CH$_3$ | 103–108 | 1725, 1593, 1435, 1213, 1090, 1067, 1021, 822, 759 |
| 80 | 3-methyl-2-quinolyl | O | CH$_3$ | CH$_3$ | | |
| 81 | 3-methyl-2-quinolyl | S | CH$_3$ | CH$_3$ | | |
| 82 | 4-methyl-2-quinolyl | O | CH$_3$ | CH$_3$ | 137–139 | 1722, 1605, 1337, 1184, 1011, 757 |
| 83 | 4-methyl-2-quinolyl | S | CH$_3$ | CH$_3$ | | |
| 84 | 4-ethyl-2-quinolyl | O | CH$_3$ | CH$_3$ | | |
| 85 | 4-ethyl-2-quinolyl | S | CH$_3$ | CH$_3$ | | |
| 86 | 4-phenyl-2-quinolyl | O | CH$_3$ | CH$_3$ | | |
| 87 | 4-phenyl-2-quinolyl | S | CH$_3$ | CH$_3$ | | |
| 88 | 6-methyl-2-quinolyl | O | CH$_3$ | CH$_3$ | | |
| 89 | 6-methyl-2-quinolyl | S | CH$_3$ | CH$_3$ | | |
| 90 | 6-chloro-2-quinolyl | O | CH$_3$ | CH$_3$ | | |
| 91 | 6-chloro-2-quinolyl | S | CH$_3$ | CH$_3$ | | |
| 92 | 8-methyl-2-quinolyl | O | CH$_3$ | CH$_3$ | | |
| 93 | 8-methyl-2-quinolyl | S | CH$_3$ | CH$_3$ | | |
| 94 | 8-chloro-2-quinolyl | O | CH$_3$ | CH$_3$ | | |
| 95 | 8-chloro-2-quinolyl | S | CH$_3$ | CH$_3$ | | |
| 96 | 4-ethoxycarbonyl-2-quinolyl | O | CH$_3$ | CH$_3$ | | |
| 97 | 4-ethoxycarbonyl-2-quinolyl | S | CH$_3$ | CH$_3$ | | |
| 98 | 3,4-dimethyl-2-quinolyl | O | CH$_3$ | CH$_3$ | | |
| 99 | 3,4-dimethyl-2-quinolyl | S | CH$_3$ | CH$_3$ | | |
| 100 | 4-methyl-8-methoxy-2-quinolyl | O | CH$_3$ | CH$_3$ | | |
| 101 | 4-methyl-8-methoxy-2-quinolyl | S | CH$_3$ | CH$_3$ | | |
| 102 | 4-phenyl-8-ethoxy-2-quinolyl | O | CH$_3$ | CH$_3$ | | |
| 103 | 4-phenyl-8-ethoxy-2-quinolyl | S | CH$_3$ | CH$_3$ | | |
| 104 | 4-methyl-8-chloro-2-quinolyl | O | CH$_3$ | CH$_3$ | | |
| 105 | 4-methyl-8-chloro-2-quinolyl | S | CH$_3$ | CH$_3$ | | |
| 106 | 4-methyl-8-fluoro-2-quinolyl | O | CH$_3$ | CH$_3$ | | |
| 107 | 4-methyl-8-fluoro-2-quinolyl | S | CH$_3$ | CH$_3$ | | |
| 108 | 4-quinolyl | O | CH$_3$ | CH$_3$ | | |
| 109 | 4-quinolyl | S | CH$_3$ | CH$_3$ | | |
| 110 | 2-methyl-4-quinolyl | O | CH$_3$ | CH$_3$ | | |
| 111 | 2-methyl-4-quinolyl | S | CH$_3$ | CH$_3$ | | |
| 112 | 2-trichloromethyl-4-quinolyl | O | CH$_3$ | CH$_3$ | | |
| 113 | 2-trichloromethyl-4-quinolyl | S | CH$_3$ | CH$_3$ | | |
| 114 | 2-trifluoromethyl-2-quinolyl | O | CH$_3$ | CH$_3$ | | |
| 115 | 2-trifluoromethyl-2-quinolyl | S | CH$_3$ | CH$_3$ | | |
| 116 | 2-iso-propyl-4-quinolyl | O | CH$_3$ | CH$_3$ | | |
| 117 | 2-iso-propyl-4-quinolyl | S | CH$_3$ | CH$_3$ | | |
| 118 | 2-n-pentyl-4-quinolyl | O | CH$_3$ | CH$_3$ | | |
| 119 | 2-n-pentyl-4-quinolyl | S | CH$_3$ | CH$_3$ | | |
| 120 | 2-phenyl-4-quinolyl | O | CH$_3$ | CH$_3$ | | |
| 121 | 2-phenyl-4-quinolyl | S | CH$_3$ | CH$_3$ | | |
| 122 | 2-methoxycarbonyl-4-quinolyl | O | CH$_3$ | CH$_3$ | | |
| 123 | 2-methoxycarbonyl-4-quinolyl | S | CH$_3$ | CH$_3$ | | |
| 124 | 2,6-dimethyl-4-quinolyl | O | CH$_3$ | CH$_3$ | | |
| 125 | 2,6-dimethyl-4-quinolyl | S | CH$_3$ | CH$_3$ | | |
| 126 | 2-methyl-6-chloro-4-quinolyl | O | CH$_3$ | CH$_3$ | | |
| 127 | 2-methyl-6-chloro-4-quinolyl | S | CH$_3$ | CH$_3$ | | |
| 128 | 2-methyl-6-fluoro-4-quinolyl | O | CH$_3$ | CH$_3$ | | |
| 129 | 2-methyl-6-fluoro-4-quinolyl | S | CH$_3$ | CH$_3$ | | |
| 130 | 8-quinolyl | O | CH$_3$ | CH$_3$ | | |
| 131 | 8-quinolyl | S | CH$_3$ | CH$_3$ | | |
| 132 | 2-methyl-8-quinolyl | O | CH$_3$ | CH$_3$ | | |
| 133 | 2-methyl-8-quinolyl | S | CH$_3$ | CH$_3$ | | |
| 134 | 5,7-dichloro-8-quinolyl | O | CH$_3$ | CH$_3$ | 120–122 | 1730, 1062, 1009, 793 742 |
| 135 | 5,7-dichloro-8-quinolyl | S | CH$_3$ | CH$_3$ | | |
| 136 | 4,6-dimethyl-2-pyrimidinyl | O | CH$_3$ | CH$_3$ | | |
| 137 | 4,6-dimethyl-2-pyrimidinyl | S | CH$_3$ | CH$_3$ | | |
| 138 | 4-trifluoromethyl-2-pyrimidinyl | O | CH$_3$ | CH$_3$ | | |
| 139 | 4-trifluoromethyl-2-pyrimidinyl | S | CH$_3$ | CH$_3$ | | |
| 140 | 4,5,6-trimethyl-2-pyrimidinyl | O | CH$_3$ | CH$_3$ | | |
| 141 | 4,5,6-trimethyl-2-pyrimidinyl | S | CH$_3$ | CH$_3$ | | |
| 142 | 4-benzyl-6-methyl-2-pyrimidinyl | O | CH$_3$ | CH$_3$ | | |

TABLE 1-continued

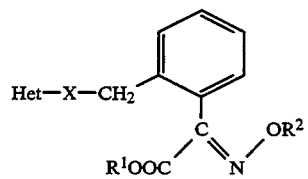

| No. | Het | X | R¹ | R² | mp (°C.) | IR (cm⁻¹) |
|---|---|---|---|---|---|---|
| 143 | 4-benzyl-6-methyl-2-pyrimidinyl | S | CH₃ | CH₃ | | |
| 144 | 4-methyl-6-phenyl-2-pyrimidinyl | O | CH₃ | CH₃ | | |
| 145 | 4-methyl-6-phenyl-2-pyrimidinyl | S | CH₃ | CH₃ | | |
| 146 | 4,6-dimethyl-5-chloro-2-pyrimidinyl | O | CH₃ | CH₃ | | |
| 147 | 4,6-dimethyl-5-chloro-2-pyrimidinyl | S | CH₃ | CH₃ | | |
| 148 | 2,6-dimethyl-4-pyrimidinyl | O | CH₃ | CH₃ | | |
| 149 | 2,6-dimethyl-4-pyrimidinyl | S | CH₃ | CH₃ | | |
| 150 | 2,6-bis-(trifluoromethyl)-4-pyrimidinyl | O | CH₃ | CH₃ | | |
| 151 | 2,6-bis-(trifluoromethyl)-4-pyrimidinyl | S | CH₃ | CH₃ | | |
| 152 | 2-chloromethyl-6-metyhl-4-pyrimidinyl | O | CH₃ | CH₃ | | |
| 153 | 2-chloromethyl-6-methyl-4-pyrimidinyl | S | CH₃ | CH₃ | | |
| 154 | 2-methyl-6-chloromethyl-4-pyrimidinyl | O | CH₃ | CH₃ | | |
| 155 | 2-methyl-6-chloromethyl-4-pyrimidinyl | S | CH₃ | CH₃ | | |
| 156 | 2-iso-propyl-6-methyl-4-pyrimidinyl | O | CH₃ | CH₃ | | |
| 157 | 2-iso-propyl-6-methyl-4-pyrimidinyl | S | CH₃ | CH₃ | | |
| 158 | 2-iso-propyl-6-chloromethyl-4-pyrimidinyl | O | CH₃ | CH₃ | | |
| 159 | 2-iso-propyl-6-chloromethyl-4-pyrimidinyl | S | CH₃ | CH₃ | | |
| 160 | 2-cyclo-propyl-6-chloromethyl-4-pyrimidinyl | O | CH₃ | CH₃ | | |
| 161 | 2-cyclo-propyl-6-chloromethyl-4-pyrimidinyl | S | CH₃ | CH₃ | | |
| 162 | 2-cyclo-propyl-6-methyl-4-pyrimidinyl | O | CH₃ | CH₃ | | |
| 163 | 2-cyclo-propyl-6-methyl-4-pyrimidinyl | S | CH₃ | CH₃ | | |
| 164 | 2-methyl-6-methoxymethyl-4-pyrimidinyl | O | CH₃ | CH₃ | | |
| 165 | 2-methyl-6-methoxymethyl-4-pyrimidinyl | S | CH₃ | CH₃ | | |
| 166 | 2-iso-propyl-6-methoxymethyl-4-pyrimidinyl | O | CH₃ | CH₃ | | |
| 167 | 2-iso-propyl-6-methoxymethyl-4-pyrimidinyl | S | CH₃ | CH₃ | | |
| 168 | 2-phenyl-4-pyrimidinyl | O | CH₃ | CH₃ | | |
| 169 | 2-phenyl-4-pyrimidinyl | S | CH₃ | CH₃ | | |
| 170 | 3,5-dimethyl-4-pyrimidinyl | O | CH₃ | CH₃ | | |
| 171 | 3,5-dimethyl-4-pyrimidinyl | S | CH₃ | CH₃ | | |
| 172 | 2-methylthio-6-trifluoromethyl-4-pyrimidinyl | O | CH₃ | CH₃ | | |
| 173 | 2-methylthio-6-trifluoromethyl-4-pyrimidinyl | S | CH₃ | CH₃ | | |
| 174 | 2-methylthio-5-chloro-6-trifluoromethyl-4-pyrimidinyl | O | CH₃ | CH₃ | | |
| 175 | 2-methylthio-5-chloro-6-trifluoromethyl-4-pyrimidinyl | S | CH₃ | CH₃ | | |
| 176 | 2-methylthio-5-n-octyl-6-methyl-4-pyrimidinyl | O | CH₃ | CH₃ | | |
| 177 | 2-methylthio-5-n-octyl-6-methyl-4-pyrimidinyl | S | CH₃ | CH₃ | | |
| 178 | 2-methyl-6-trifluoromethyl-4-pyrimidinyl | O | CH₃ | CH₃ | | |
| 179 | 2-methyl-6-trifluoromethyl-4-pyrimidinyl | S | CH₃ | CH₃ | 60-61 | |
| 180 | 2-n-propyl-6-trifluoromethyl-4-pyrimidinyl | O | CH₃ | CH₃ | | |
| 181 | 2-n-propyl-6-trilfuoromethyl-4-pyrimidinyl | S | CH₃ | CH₃ | | |
| 182 | 2-iso-propyl-6-trifluoromethyl-4-pyrimidinyl | O | CH₃ | CH₃ | | |
| 183 | 2-iso-propyl-6-trifluoromethyl-4-pyrimidinyl | S | CH₃ | CH₃ | | |
| 184 | 2-tert.-butyl-6-trifluoromethyl-4-pyrimidinyl | O | CH₃ | CH₃ | | |
| 185 | 2-tert.-butyl-6-trifluoromethyl-4-pyrimidinyl | S | CH₃ | CH₃ | | |
| 186 | 2-methyl-5-chloro-6-trifluoromethyl-4-pyrimidinyl | O | CH₃ | CH₃ | | |
| 187 | 2-methyl-5-chloro-6-trifluoromethyl-4-pyrimidinyl | S | CH₃ | CH₃ | | |
| 188 | 2-n-propyl-5-chloro-6-trifluoromethyl-4-pyrimidinyl | O | CH₃ | CH₃ | | |
| 189 | 2-n-propyl-5-chloro-6-trifluoromethyl-4-pyrimidinyl | S | CH₃ | CH₃ | | |
| 190 | 2-iso-propyl-5-chloro-6-trifluoromethyl-4-pyrimidinyl | O | CH₃ | CH₃ | | |
| 191 | 2-iso-propyl-5-chloro-6-trifluoromethyl-4-pyrimidinyl | S | CH₃ | CH₃ | | |
| 192 | 2-tert.-butyl-5-chloro-6-trifluoromethyl-4-pyrimidinyl | O | CH₃ | CH₃ | | |
| 193 | 2-tert.-butyl-5-chloro-6-trifluoromethyl-4-pyrimidinyl | S | CH₃ | CH₃ | | |
| 194 | 2-pyrimidinyl | S | CH₃ | CH₃ | | |
| 195 | 6-methyl-2-pyridyl | O | H | CH₃ | | |
| 196 | 6-methyl-2-pyridyl | O | CH₃ | H | | |
| 197 | 6-methyl-2-pyridyl | S | CH₃ | H | | |
| 198 | 6-methyl-2-pyridyl | O | C₂H₅ | C₂H₅ | | |
| 199 | 6-methyl-2-pyridyl | S | C₂H₅ | C₂H₅ | | |
| 200 | 6-methyl-2-pyridyl | O | CH₃ | C₂H₅ | | |
| 201 | 6-methyl-2-pyridyl | S | CH₃ | C₂H₅ | | |
| 202 | 6-methyl-2-pyridyl | O | CH₃ | n-C₃H₇ | | |
| 203 | 6-methyl-2-pyridyl | O | CH₃ | i-C₃H₇ | | |

TABLE 1-continued

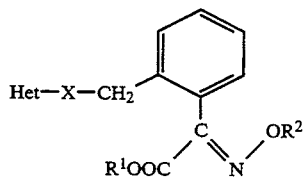

| No. | Het | X | R¹ | R² | mp (°C.) | IR (cm⁻¹) |
|---|---|---|---|---|---|---|
| 204 | 6-methyl-2-pyridyl | O | CH₃ | C₄H₉ | | |
| 205 | 6-methyl-2-pyridyl | O | CH₃ | C₅H₁₁ | | |
| 206 | 6-cyclopropyl-2-pyridyl | O | CH₃ | CH₃ | | |
| 207 | 6-cyclopropyl-2-pyridyl | S | CH₃ | CH₃ | | |
| 208 | 2-pyrazinyl | O | CH₃ | CH₃ | | |
| 209 | 2-pyrazinyl | S | CH₃ | CH₃ | | |
| 210 | 6-chloro-2-pyrazinyl | O | CH₃ | CH₃ | | |
| 211 | 6-chloro-2-pyrazinyl | S | CH₃ | CH₃ | | |
| 212 | 5-methyl-2-pyrazinyl | O | CH₃ | CH₃ | | |
| 213 | 5-methyl-2-pyrazinyl | S | CH₃ | CH₃ | | |
| 214 | 3-pyridazinyl | O | CH₃ | CH₃ | | |
| 215 | 3-pyridazinyl | S | CH₃ | CH₃ | | |
| 216 | 5-chloro-3-pyridazinyl | O | CH₃ | CH₃ | | |
| 217 | 5-chloro-3-pyridazinyl | S | CH₃ | CH₃ | | |
| 218 | 2-thienyl | O | CH₃ | CH₃ | | |
| 219 | 2-thienyl | S | CH₃ | CH₃ | | |
| 220 | 3-thienyl | O | CH₃ | CH₃ | | |
| 221 | 3-thienyl | S | CH₃ | CH₃ | | |
| 222 | 4-chloro-3-thienyl | O | CH₃ | CH₃ | | |
| 223 | 4-chloro-3-thienyl | S | CH₃ | CH₃ | | |
| 224 | 2-chloro-3-thienyl | O | CH₃ | CH₃ | | |
| 225 | 2-chloro-3-thienyl | S | CH₃ | CH₃ | | |
| 226 | 5-chloro-3-thienyl | O | CH₃ | CH₃ | | |
| 227 | 5-chloro-3-thienyl | S | CH₃ | CH₃ | | |
| 228 | 2-quinoxalinyl | O | CH₃ | CH₃ | | |
| 229 | 2-quinoxalinyl | S | CH₃ | CH₃ | | |
| 230 | 3-methyl-2-quinoxalinyl | O | CH₃ | CH₃ | | |
| 231 | 3-methyl-2-quinoxalinyl | S | CH₃ | CH₃ | | |
| 232 | 7,8-dimethyl-2-quinoxalinyl | O | CH₃ | CH₃ | | |
| 233 | 7,8-dimethyl-2-quinoxalinyl | S | CH₃ | CH₃ | | |
| 234 | 7,8-dichloro-2-quinoxalinyl | O | CH₃ | CH₃ | | |
| 235 | 7,8-dichloro-2-quinoxalinyl | S | CH₃ | CH₃ | | |
| 236 | 7-methyl-2-quinoxalinyl | O | CH₃ | CH₃ | | |
| 237 | 7-methyl-2-quinoxalinyl | S | CH₃ | CH₃ | | |
| 238 | 8-methyl-2-quinoxalinyl | O | CH₃ | CH₃ | | |
| 239 | 8-methyl-2-quinoxalinyl | S | CH₃ | CH₃ | | |
| 240 | 7-methoxy-2-quinoxalinyl | O | CH₃ | CH₃ | | |
| 241 | 7-methoxy-2-quinoxalinyl | S | CH₃ | CH₃ | | |
| 242 | 3-phenyl-5-isoxazolyl | O | CH₃ | CH₃ | | |
| 243 | 3-phenyl-5-isoxzazolyl | S | CH₃ | CH₃ | | |
| 244 | 2-benzoxazolyl | O | CH₃ | CH₃ | | |
| 245 | 2-benzothiazolyl | O | CH₃ | CH₃ | | |
| 246 | 6-methyl-2-benzothiazolyl | S | CH₃ | CH₃ | 86–88 | |
| 247 | 4-chloro-2-benzothiazolyl | S | CH₃ | CH₃ | 141–143 | 1732, 1455, 1299, 1225, 1059, 1101, 766 |
| 248 | 6-chloro-2-benzothiazolyl | S | CH₃ | CH₃ | 103–100 | 1737, 1439, 1302, 1061, 1009, 815 |
| 249 | 6-ethoxy-2-benzothiazolyl | S | CH₃ | CH₃ | 91–93 | |
| 250 | 5-trifluoromethyl-2-benzothiazolyl | S | CH₃ | CH₃ | 93–95 | |
| 251 | 1,2-benzothiazol-7-yl | O | CH₃ | CH₃ | 120–123 | |
| 252 | 4,8-dimethyl-2-quinolyl | S | CH₃ | CH₃ | 108–110 | |
| 253 | 4,8-dimethyl-2-quinolyl | O | CH₃ | CH₃ | 109–112 | |
| 254 | 6-iso-butyl-2-pyridyl | O | CH₃ | CH₃ | 84–86 | |
| 255 | 3-cyano-6-iso-butyl-2-pyridyl | O | CH₃ | CH₃ | 83–86 | |
| 256 | 2-pyrimidinyl | S | CH₃ | CH₃ | 96–98 | 1727, 1551, 1378, 1217, 1200, 1069, 1020, 756 |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases: Erysiphe graminis in cereals, Erysiphe cichoracearum and Sphaerotheca fuliginea in cucurbits, Podosphaera leucotricha in apples, Uncinula necator in vines, Puccinia species in cereals, Rhizoctonia species in cotton and lawns, Ustilago species in cereals and sugar cane, Venturia inaequalis (scab) in apples, Helminthosporium species in cereals, Septoria nodorum in wheat, Botrytis cinerea (gray mold) in strawberries and grapes, Cercospora arachidicola in groundnuts, Pseudocercosporella herpotrichoides in wheat and barley, Pyricularia oryzae in rice, Phytophthora infestans in potatoes and tomatoes, Fusarium and Verticillium species in various plants, Plasmopara viticola in grapes, Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in Known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), Ketones (e.g., cyclohexanone), amines (e.g., ethanolamine, dimethylformamide), and water; carriers such as ground natural minerals (e.g., Kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt. %, of active ingredient. The application rates are from 0.02 to 3 kg or more of active ingredient per hectare, depending on the type of effect desired. The novel compounds may also be used for protecting materials, for example against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 8 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 12 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 5 is intimately mixed with 97 parts by weight of particulate kaolin. A dust is obtained containing 3% by weight of the active ingredient.

VII. 30 parts by weight of compound no. 8 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 12 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides, ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis(thiocarbamyl) disulfide; nitro derivatives, such as dinitro(1-methylheptyl)-phenyl crotonate, 2-sec-butyl-4,6-dinitrophenyl 3,3-dimethylacrylate, 2-sec-butyl-4,6-dinitrophenyl isopropylcarbonate and diisopropyl 5-nitroisophthalate; heterocyclic substances, such as 2-heptadecylimidazol-2-yl acetate, 2,4-dichloro- 6-(o-chloroanilino)-s-triazine, O,O-diethyl phthalimidophosphonothioate, 5-amino-1-[-bis-(dimethylamino)-phosphinyl]-3-phenyl-1,2,4-triazole, 2,3-dicyano-1,4-dithioanthraquinone, 2-thio-1,3-dithio[4,5-b]quinoxaline, methyl 1-(butylcarbamyl)-2-benzimidazolecarbamate, 2-methoxycarbonylaminobenzimidazole, 2-(fur-2-yl)-benzimidazole, 2-(thiazol-4-yl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline and its copper salt, 2,3-dihydro-5-carboxanilido- 6-methyl-1,4-oxathiyne, 2,3-dihydro-5-carboxanilido-6-methyl-1,4-oxathiyne 4,4-dioxide, 2-methyl furan-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-diethylfuran-3-carboxamide, 2-methylbenzanilide, 2-iodobenzanilide, N-formyl-N-morpholine-2,2,2-trichloroethylacetal, piperazine-1,4-diylbis-(1-(2,2,2-trichloroethyl)-formamide), 1-(3,4-dichloroanilino)-1-formylamino-2,2,2-trichloroethane, 2,6-dimethyl-N-tridecylmorpholine and its salts, 2,6-dimethyl-N-cyclododecylmorpholine and its salts, N-[3- (p-tert.-butylphenyl)-2-methylpropyl]-cis-2,6-dimethylmorpholine, N-[3- (p-tert.-butylphenyl)-2-methylpropyl]-piperidine, 1-[2- (2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol, 1-(4-phenylphenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl- (2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis- (3-methoxycarbonyl-2-thioureido)-benzene, and various fungicides, such as dodecylguanidine acetate, 3-[3-(3,5-dimethyl-2-oxycyclohexyl)-2-hydroxyethyl]-glutaramide, hexachlorobenzene, DL-methyl-N-(2,6-dimethylphenyl)-N-fur-2-yl alanate, methyl DL-N-(2,6-dimethylphenyl)-N-(2'-methoxyacetyl)-alanate, N-(2,6-dimethylphenyl)-N-chloroacetyl-DL-2-aminobutyrolactone, methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3- (3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-α-(1H-1,2,4-triazol-1-ylmethyl)-benzhydryl alcohol, N-(3-chloro-2,6-dinitro-4-trifluoromethylphenyl)-5-trifluoromethyl-3-chloro-2-aminopyridine, and 1-((bis-(4-fluorophenyl)-methylsilyl)-methyl)-1H-1,2,4-triazole.

For comparison purposes, 2-(phenyloxymethyl)-phenylglyoxylic acid methyl ester-0-methyloxime (A)-disclosed in EP 253,213-was used.

USE EXAMPLE 1

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients nos. 2, 3, 5, 8, 9, 12, 27, 50, 246, 249, 250 and 254, applied as 0.05, 0.025 and 0.0125 wt. % spray liquors, have a better fungicidal action (100%) than prior art comparative agent A (90%).

USE EXAMPLE 2

Action on Phytophthora infestans

Leaves of potted tomatoes of the "Große Fleischtomate" variety were sprayed with aqueous liquors containing (dry basis) 80 wt. % of active ingredient and 20 wt. % of emulsifier. 24 hours later, the leaves were infected with a zoospore suspension of the fungus Phytophthora infestans. The plants were then set up in a water vapor-saturated chamber at from 16° to 18° C. After 6 days, the disease had spread to such an extent on the untreated (infected) control plants that the fungicidal action of the compounds was able to be assessed.

The results show that active ingredient no. 2, applied as a 0.025% spray liquor, has a better fungicidal action (90%) than prior art comparative agent A (55%).

USE EXAMPLE 3

Action on Pyrenophora teres

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus Pyrenophora teres, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients nos. 5, 8, 12, 13, 50, 248 and 257, applied as 0.05% spray liquors, have a better fungicidal action (97%) than prior art comparative agent A (55%).

We claim:
1. Oxime ether derivatives of the formula I

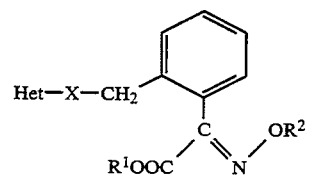

wherein $R^1$ and $R^2$ are each hydrogen or $C_1$-$C_5$-alkyl, Het is pyridyl substituted by halogen, $C_1$-$C_8$-alkyl, $C_3$-$C_6$-cycloalkyl, $C_1$-$C_2$-haloalkyl, $C_1$-$C_4$-alkoxy, $C_1$-$C_4$-alkyl, $C_1$-$C_4$-alkoxy, phenyl, benzyl, 2-phenylethyl, 3-phenylpropyl, 4-phenylbutyl, $C_1$-$C_4$-alkylcarbonyl, $C_1$-$C_4$-alkoxycarbonyl or cyano, and X is oxygen, and their plant-tolerated acid addition salts, metal complexes and N-oxides.

2. A process for combating fungi, wherein the fungi, or the materials, plants, seed or the soil threatened by fungus attack are treated with a fungicidally effective amount of a compound of the formula I

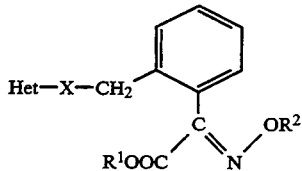
(I)

wherein $R^1$ and $R^2$ are each hydrogen or $C_1$-$C_5$-alkyl, Het is pyridyl substituted by halogen, $C_1$-$C_8$-alkyl, $C_3$-$C_6$-cycloalkyl, $C_1$-$C_2$-haloalkyl, $C_1$-$C_4$-alkyloxy, $C_1$-$C_4$-alkoxy-$C_1$-$C_4$-alkyl, phenyl, benzyl, 2-phenylethyl, 3-phenylpropyl, 4-phenylbutyl, $C_1$-$C_4$-alkylcarbonyl, $C_1$-$C_4$-alkoxycarbonyl or cyano, and X is oxygen, and their plant-tolerated acid addition salts, metal complexes and N-oxides.

3. A fungicide containing an inert carrier and a fungicidally effective amount of a compound of the formula I

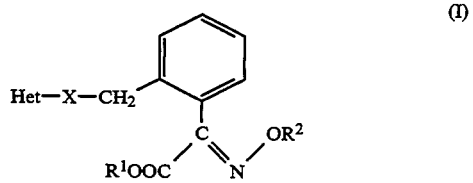
(I)

wherein $R^1$ and $R^2$ are each hydrogen or $C_1$-$C_5$-alkyl, Het is pyridyl substituted by halogen, $C_1$-$C_8$-alkyl, $C_3$-$C_6$-cycloalkyl, $C_1$-$C_2$-haloalkyl, $C_1$-$C_4$-alkyloxy, $C_1$-$C_4$-alkoxy-$C_1$-$C_4$-alkyl, phenyl, benzyl, 2-phenylethyl, 3-phenylpropyl, 4-phenylbutyl, $C_1$-$C_4$-alkylcarbonyl, $C_1$-$C_4$-alkoxycarbonyl or cyano, and X is oxygen, and their plant-tolerated acid addition salts, metal complexes and N-oxides.

4. A compound of the formula I as set forth in claim 1, wherein $R^1$ and $R^2$ are each methyl, Het is 6-methyl-2-pyridyl and X is oxygen.

5. A compound of the formula I as set forth in claim 1, wherein $R^1$ and $R^2$ are each methyl, Het is 6-isopropyl-2-pyridyl and X is oxygen.

6. A compound of the formula I as set forth in claim 1, wherein $R^1$ and $R^2$ are each methyl, Het is 6-tert-butyl-2-pyridyl and X is oxygen.

* * * * *